United States Patent
Compagnon et al.

(10) Patent No.: US 10,832,801 B2
(45) Date of Patent: Nov. 10, 2020

(54) METHOD FOR SEQUENCING OLIGOSACCHARIDES

(71) Applicants: CENTRE NATIONAL DE LA RECHERCHE SCIENTIFIQUE, Paris (FR); UNIVERSITE CLAUDE BERNARD LYON 1, Villeurbanne (FR)

(72) Inventors: Isabelle Compagnon, Lyons (FR); Baptiste Schindler, Villeurbanne (FR)

(73) Assignees: CENTRE NATIONAL DE LA RECHERCHE SCIENTIFIQUE, Paris (FR); UNIVERSITÉ CLAUDE BERNARD LYON 1, Villeurbanne (FR)

(*) Notice: Subject to any disclaimer, the term of this patent is extended or adjusted under 35 U.S.C. 154(b) by 219 days.

(21) Appl. No.: 16/094,129

(22) PCT Filed: Apr. 14, 2017

(86) PCT No.: PCT/EP2017/059050
§ 371 (c)(1),
(2) Date: Oct. 16, 2018

(87) PCT Pub. No.: WO2017/182404
PCT Pub. Date: Oct. 26, 2017

(65) Prior Publication Data
US 2019/0206516 A1    Jul. 4, 2019

(30) Foreign Application Priority Data
Apr. 18, 2016    (FR) ...................................... 16 53425

(51) Int. Cl.
*G16C 20/20*     (2019.01)
*G01N 21/35*     (2014.01)
(Continued)

(52) U.S. Cl.
CPC ............ *G16C 20/20* (2019.02); *A61K 31/702* (2013.01); *C07H 3/06* (2013.01); *C07H 13/02* (2013.01);
(Continued)

(58) Field of Classification Search
None
See application file for complete search history.

(56) References Cited

U.S. PATENT DOCUMENTS 8,293,084 B2    10/2012    Rapp et al.

FOREIGN PATENT DOCUMENTS

| WO | 0187832 A2 | 11/2001 |
| WO | 0187833 A2 | 11/2001 |
| WO | 2014007730 A1 | 1/2014 |

OTHER PUBLICATIONS

Pikulski et al., "Sequencing and characterization of oligosaccharides using infrared multiphoton dissociation and boronic acid derivatization in a quadrupole ion trap.", J Am Soc Mass Spectrom. Dec. 2007;18(12):2094-106. Epub Sep. 14, 2007; DOI: 10.1016/j.jasms.2007.09.005.
(Continued)

*Primary Examiner* — Xiaoyun R Xu
(74) *Attorney, Agent, or Firm* — BCF LLP

(57) ABSTRACT

The present invention concerns a method for sequencing oligosaccharides, which makes it possible to identify the primary sequence of an oligosaccharide of unknown structure, including its monosaccharide composition, the position (regiochemistry) and configuration (stereochemistry) of glycosidic bonds, the nature and position of functional modifications, and its branched structure, particularly including the identification of the reducing end.

8 Claims, 2 Drawing Sheets

(51) Int. Cl.
　　　G01N 33/66　　(2006.01)
　　　C07H 3/06　　(2006.01)
　　　A61K 31/702　　(2006.01)
　　　C07H 13/02　　(2006.01)
　　　G01N 21/3504　　(2014.01)
　　　H01J 49/00　　(2006.01)

(52) U.S. Cl.
　　　CPC ......... *G01N 21/35* (2013.01); *G01N 21/3504* (2013.01); *G01N 33/66* (2013.01); *H01J 49/0054* (2013.01); *H01J 49/0059* (2013.01); *H01J 49/0068* (2013.01); *H01J 49/0072* (2013.01)

(56) References Cited

OTHER PUBLICATIONS

Stefan et al., "Differentiation of closely related isomers: application of data mining techniques in conjunction with variable wavelength infrared multiple photon dissociation mass spectrometry for identification of glucose-containing iisaccharide ions.", Anal. Chem., 2011, 83 (22), pp. 8468-8476, DOI: 10.1021/ac2017103.

Schindler et al., "Distinguishing isobaric phosphated and sulfated carbohydrates by coupling of mass spectrometry with gas phase vibrational spectroscopy", Physical Chemistry Chemical Physics 16(40) •Aug. 2014, DOI: 10.1039/C4CP02898H.

Wu et al, "Employment of Tandem Mass Spectrometry for the Accurate and Specific Identification of Oligosaccharide Structures", Anal. Chem., 2012, 84 (17), pp. 7456-7462, DOI: 10.1021/ac301398h, Publication Date (Web): Aug. 6, 2012.

Patrick et al., "Insights into the fragmentation pathways of gas-phase protonated sulfoserine", International Journal of Mass Spectrometry, vol. 379, Mar. 15, 2015, pp. 26-32, https://doi.org/10.1016/j.ijms.2014.12.001.

Ly et al., "The proteoglycan bikunin has a defined sequence", Nat Chem Biol. Nov. 2011; 7(11): 827-833, Published online Oct. 9, 2011. doi: 10.1038/nchembio.673.

Both et al., "Discrimination of epimeric glycans and glycopeptides using IM-MS and its potential for carbohydrate sequencing", Nature Chemistry vol. 6, pp. 65-74 (2014), https://doi.org/10.1038/nchem.1817.

Gaye et al., "Multidimensional Analysis of 16 Glucose Isomers by Ion Mobility Spectrometry", Anal. Chem., 2016, 88 (4), pp. 2335-2344, DOI: 10.1021/acs.analchem.5b04280.

Nagy et al., "Monosaccharide Identification as a First Step toward de Novo Carbohydrate Sequencing: Mass Spectrometry Strategy for the Identification and Differentiation of Diastereomeric and Enantiomeric Pentose Isomers", Anal Chem. Apr. 21, 2015;87(8):4566-71. doi: 10.1021/acs.analchem.5b00760. Epub Apr. 9, 2015.

Hofmann et al., "Identification of carbohydrate anomers using ion mobility-mass spectrometry", Nature. Oct. 3, 2015;526(7572):241-4. doi: 10.1038/nature15388. Epub Sep. 30, 2015.

Reaping the Benefits of Genomic and Proteomic Research, Intellectual Property Rights, Innovation, and Public Health (2006), ISBN: 0-309-65523-4, 188 pages, 6×9, (2006), https://doi.org/10.17226/11487.

Gaye M. et al., "Investigating carbohydrate isomers by IMS-CID-IMS-MS: precursor and fragment ion cross-sections", Analyst. Oct. 21, 2015;140(20):6922-32. doi: 10.1039/c5an00840a. Epub Aug. 26, 2015.

Polfer et al., "Vibrational spectroscopy of bare and solvated ionic complexes of biological relevance", Feb. 24, 2009, Mass Spec Rev 28:468-494, 2009, lhttps://doi.org/10.1002/mas.20215.

"Transforming Glycoscience: A Roadmap for the Future", Washington (DC): National Academies Press (US); 2012. ISBN: Paperback: 978-0-309-26083-1.

Furukawa et al., "Recent Advances in Cellular Glycomic Analyses", Biomolecules. Mar. 2013; 3(1): 198-225, doi: 10.3390/biom3010198.

Nagy et al., "Complete Hexose Isomer Identification with Mass Spectrometry", J. Amer. Soc. Mass Spectrom. 2015, 26, 677-685.

Li et al., "Ion mobility mass spectrometry analysis of isomeric disaccharide precursor, product and cluster ions", Rapid Comm. Mass Spectrom. 2013, 27, 2699-2709, https://doi.org/10.1002/rcm.6720.

Domon et al., "A systematic nomenclature for carbohydrate fragmentations in FAB-MS/MS spectra of glycoconjugates", Glycoconjugate Journal, 1988, vol. 5, pp. 397-409.

Zaia J., "Mass Spectrometry and Glycomics", OMICS. Aug. 2010;14(4):401-18. doi: 10.1089/omi.2009.0146.

METHOD FOR SEQUENCING OLIGOSACCHARIDES

CROSS-REFERENCE TO RELATED APPLICATIONS

This application is a national phase filing under 35 U.S.C. § 371 of International Application No. PCT/EP2017/059050 filed on Apr. 14, 2017, which claims benefit of priority from French Patent Application No. 1653425 filed Apr. 18, 2016, the contents of which are hereby incorporated by reference in their entirety.

FIELD OF INVENTION

The present invention concerns a method for sequencing oligosaccharides, which makes it possible to identify the primary sequence of oligosaccharides of unknown structure, including its monosaccharide composition, the position (regiochemistry) and configuration (stereochemistry) of glycosidic bonds, the nature and position of functional modifications, and its branched structure, particularly including the identification of the reducing end.

STATE OF THE ART

Since the 1990s, the industrial-scale sequencing of proteins and the genome has had a significant economic and scientific impact and has revolutionized modern biology. However, there is no commercial method for the systematic sequencing of saccharides, owing to their greater structural complexity relative to other classes of biopolymers. The lack of analytical tools adapted to the specific molecular structure of saccharides is an obstacle to the development of glycoscience.

Two approaches can be considered for resolving the structure of biomolecules: either an overall approach to the structure (by nuclear magnetic resonance (NMR), for example), or a "sequencing"—type approach consisting in reduction of the polymer to subunits and analysis of the structure of these subunits. Ideally, the structural detail of the molecule of interest is preserved in its subunits and can be found by analysis of the latter. This precondition is confirmed, for example, in the case of protein sequencing by mass spectrometry.

In the case of sugars, several methods can reduce a saccharide to subunits, including enzymatic digestion, chemical hydrolysis, and various methods of fragmentation by mass spectrometry.

The main technology described in relation to oligosaccharide sequencing is adapted from protein sequencing and relies on fragmentation and fragment analysis by mass spectrometry (Science 1999, 15, 537-542; Nature Chem. Biol. 2011, 7, 827-833). This type of analysis does not allow a determination of all the relevant structural properties of fragments, and its limitations are well known and widely referenced (Omics 2010, 14, 401-418).

More recently, several groups have proposed a combination of ion mobility with mass spectrometry (Li, H. et al., Rapid Comm. Mass Spectrom. 2013, 27, 2699-2709; Both, P. et al., Nat. Chem. 2013, 6, 65-74; Gaye, M. M. et al., Analyst, 2015, 140, 6922; Hofmann, J. et al., Nature, 2015, 526, 241). This technology was unable to establish a direct relationship between the structure of the molecule of interest and the structure of its fragments.

More recently, Nagy et al. (Anal. Chem. 2015, 87, 677-685; J. Amer. Soc. Mass Spectrom. 2015, 26, 677-685; Anal. Chem. 2016, 88, 2335-2344) describe the analysis of monosaccharides by a method of complexation with a divalent metal and a chiral reference, such as an amino acid (L-aspartic or L-serine), then mass analysis of the complexes formed by mass spectrometry. The de novo analysis envisaged by the authors requires a preliminary hydrolysis of the oligosaccharides and a sample preparation which remains to be developed.

These basic research publications concern the evaluation of techniques orthogonal to mass spectrometry, but do not allow the de novo resolution of oligosaccharide sequences of unknown structures. In particular, they do not provide the information necessary for complete sequencing of oligosaccharides, including its monosaccharide composition, the position (regiochemistry) and configuration (stereochemistry) of glycosidic bonds, the nature and position of functional modifications, and its branched structure, particularly including the identification of the reducing end.

The method according to the invention solves this problem.

The skilled person knows different methods of analysis of mono- or disaccharides by vibrational spectroscopy, notably methods where pure samples of mono- or disaccharides are prepared by means of a mass spectrometry apparatus which is used for preparation of gas-phase samples for analysis by vibrational spectroscopy, and not for their fragmentation (Stefan, S. et al., Anal. Chem. 2011, 83, 8468-8476; Schindler, B. et al., Phys. Chem. Chem. Phys. 2014, 16, 22131-22138).

DISCLOSURE OF THE INVENTION

The present invention concerns a method for sequencing oligosaccharides, characterized in that it comprises the steps of i. fragmentation of the oligosaccharides into disaccharides and monosaccharides while preserving the molecular structure of the constituents as present in the oligosaccharide to be sequenced ii. separation of each previously obtained disaccharide and monosaccharide by mass spectrometry, iii. analysis by infrared (IR) vibrational spectroscopy of each previously separated disaccharide and monosaccharide, iv. identification of the structure of each disaccharide and monosaccharide by comparison of the obtained IR spectra with a set of reference disaccharide and monosaccharide IR spectra, and v. definition of the oligosaccharide sequence by combination of the structures identified for each disaccharide and monosaccharide.

The invention also concerns a device for implementing the method.

DETAILED DESCRIPTION OF THE INVENTION

The present invention concerns a method for sequencing oligosaccharides which allows the resolution of the structure of oligosaccharides of unknown structure, in particular oligosaccharides of more than 2 monosaccharides, 3, 4, 5, 6 monosaccharides, or even more than 10 monosaccharides, up to 20 monosaccharides or more.

In the case of polysaccharides of very large structure, the sequencing can be done in several steps, with first a fragmentation into oligosaccharides of about 20 monosaccharides, which are then sequenced with the method according to the invention.

According to the invention, "sequencing" means the resolution of the monosaccharide composition, the position (regiochemistry) and configuration (stereochemistry) of glycosidic bonds, the nature and position of functional modifications, and its branched structure, particularly including the identification of the reducing end.

Step i. of fragmentation of the oligosaccharides into disaccharides and monosaccharides is particularly important since it must preserve the structure of the constituents as present in the oligosaccharide, i.e. preserve the very nature of the sugar according to the positioning and stereochemistry of hydroxyl substituents on the ring, preserve the nature and position of functional modifications and make it possible to identify the position (regiochemistry) and configuration (stereochemistry) of glycosidic bonds as well as the branched structure and the reducing end. According to a preferred embodiment of the invention, the fragmentation is achieved by mass spectrometry. Indeed, the inventors were able to show that mass spectrometry preserved the structural information of the precursor during fragmentation.

The skilled person will be able to determine the fragmentation conditions so as to preserve the structural information of the precursor, in particular by using for example the fragmentation methods integrated into commercial mass spectrometers, such as collision-induced dissociation (CID), collision-activated dissociation (CAD), surface-induced dissociation (SID), electron-transfer dissociation (ETD), electron-collision dissociation (ECD) and laser induced fragmentation, and preferably the CID method.

Mass spectrometry methods for preparing samples for IR spectroscopy (step ii.) are well known, notably as described by Schindler, B. et al. (*Phys. Chem. Chem. Phys.* 2014, 16, 22131-22138).

The skilled person will be able to determine the optimal conditions for implementing this sample preparation step: in particular, the fragment of interest (monosaccharide or disaccharide constituting the precursor oligosaccharide) will be generated by the collision-induced dissociation (CID) fragmentation method in one or more mass spectrometry steps $MS^n$, then it will be isolated by mass spectrometry preparatory to IR spectroscopy.

IR spectroscopy analysis of sugars is known to the skilled person, notably as described by Schindler, B. et al. (*Phys. Chem. Chem. Phys.* 2014, 16, 22131-22138). To distinguish the different sugars, their structure, and the position (regiochemistry) and configuration (stereochemistry) of glycosidic bonds, information relating to IR frequencies below 4000 $cm^{-1}$ will be sought in particular. For the nature and position of functional modifications, information relating to IR frequencies below 4000 $cm^{-1}$ will be sought in particular. According to a preferred embodiment of the invention, IR spectroscopy (step iii.) is performed at a wavelength ranging from 4000 to 2000 $cm^{-1}$.

The skilled person will know how to determine the optimal conditions for implementing this spectroscopy, based on the IR spectroscopy methods integrated into a mass spectrometer at his or her disposal. Different IR spectroscopy methods integrated into a mass spectrometer are described in the literature and known to the skilled person. Particular mention may be made of infrared multiphoton dissociation (IRMPD) spectroscopy, UV/IR double-resonance spectroscopy, hydrogen or helium attachment spectroscopy. Preferably, spectroscopy will be performed by the IRMPD method implemented with an ion trap, making it possible to produce fragments by mass spectrometry and analyse them with a single integrated instrumental setup, as described by Schindler, B. et al. (*Phys. Chem. Chem. Phys.* 2014, 16, 22131-22138).

The structure of each disaccharide and monosaccharide is identified by comparison of the obtained IR spectra with a previously recorded set of reference disaccharide and monosaccharide IR spectra.

Identification is made by comparison of the obtained spectroscopic fingerprint with the reference spectroscopic fingerprints, in particular by comparison of the positions and intensities of the vibrational bands in the spectral range 2000-4000 $cm^{-1}$, by any visual comparison method carried out by the operator or any computerized method known to the skilled person.

These reference spectroscopic fingerprints (reference spectra) are obtained by the same spectroscopic method as that implemented for the method according to the invention (sample preparation mass spectrometry steps ii and IR spectroscopy step iii.). They are obtained for compounds including monosaccharides (anomeric mixture), pure anomeric forms of monosaccharides (either natural or chemically modified, for example by methylation of the reducing hydroxyl group), dehydroxylated forms of monosaccharides, disaccharides and dehydroxylated forms of disaccharides. For each type of reference compound, the different known functionalized forms and their positional isomers will be analysed.

Advantageously, these reference spectra are assembled and stored in a database or library. This database can be a "physical" database where spectra printed on suitable media, particularly paper, are classified by type of sugar and stored in one place, accessible for spectra comparisons. According to a preferred embodiment of the invention, the database is a paperless database where all information on mono- and disaccharides, their structures, associated spectra, characteristic bands and their relative intensities are kept in digital form and stored on a computer medium, a computer, a server or a cloud server. In this case, the database is accessed by any suitable means of communication. The spectra obtained for the mono- and disaccharides derived from the fragmentation of the oligosaccharide to be analysed are then compared by the same "computer" means, notably by well-known data comparison methods, whether images (spectra) or values obtained from these spectra.

In the event that the database does not contain a reference spectrum associated with a particular mono- or disaccharide derived from the fragmentation of an oligosaccharide of unknown structure, the skilled person will be able to supplement the database with relevant reference monosaccharides and disaccharides, in particular by estimating the possible structures on the basis of the information obtained by mass spectrometry and IR spectroscopy.

Knowledge of the information relating to each constituent di- and monosaccharide of the oligosaccharide analysed, in particular knowledge of the position and configuration of their glycosidic bonds, makes it possible to determine the sequence of the starting oligosaccharide by combining the different structures. These combinatorial methods are described below.

In particular, the combination of the information obtained with the monosaccharides and disaccharides is necessary and sufficient to resolve the oligosaccharide structure.

The monosaccharide composition and the configuration (stereochemistry) of glycosidic bonds, the nature and position of functional modifications, and the branched structure, particularly including the identification of the reducing end of the oligosaccharide analysed, are identified by matching the spectroscopic fingerprints of the constituent monosaccharides with the reference library in the following manner:

the spectroscopic fingerprint measured for each of the constituent monosaccharides is compared with the appropriate section of the reference library, i.e. the section comprising the reference isomers corresponding to the mass of the fragment measured in step 1.

a match for the dehydroxylated fragments is obtained in the reference library of dehydroxylated monosaccharides, making it possible to identify the nature of each of the constituent monosaccharides and the position of their functional modifications if need be. The monosaccharide composition of the parent oligosaccharide and the position of functional modifications are thus obtained.

a match for the complete fragments is obtained in the reference library of standard monosaccharides and their pure anomeric forms, making it possible to identify the nature of each of the constituent monosaccharides and the position of their functional modifications if need be. The monosaccharide composition of the parent oligosaccharide and the position of functional modifications are thus obtained (information potentially redundant with the analysis of dehydroxylated fragments).

complete fragments having a match in the library of monosaccharides (anomeric mixture) are identified as reducing ends.

complete fragments having a match in the library of monosaccharides of pure anomeric form are identified as non-reducing ends and their anomeric configuration is identified.

The monosaccharide composition, the position (regiochemistry) and configuration (stereochemistry) of glycosidic bonds, the nature and position of functional modifications of the oligosaccharide, and its branched structure, particularly including the identification of the reducing end of the parent oligosaccharide, are identified by matching the spectroscopic fingerprints of the constituent disaccharides with the reference library in the following manner:

the spectroscopic fingerprint measured for each of the constituent disaccharides is compared with the appropriate section of the reference library, i.e. the section comprising the reference isomers corresponding to the mass of the fragment.

knowing the monosaccharide composition, the position of functional modifications and the anomeric configuration of bonds, the matching of the disaccharides makes it possible to identify the position of the glycosidic bond.

alternatively, the analysis of the disaccharides by matching with the reference library makes it possible to identify their monosaccharide composition, the position of functional modifications, the anomeric configuration and position of the glycosidic bond.

The invention also concerns an apparatus for sequencing oligosaccharides comprising a mass spectrometry device, an electromagnetic radiation source, a database and processing means, characterized in that it comprises a processor for controlling the steps of i. fragmentation of the oligosaccharides into disaccharides and monosaccharides while preserving the molecular structure of the constituents as present in the oligosaccharide to be sequenced ii. separation of each previously obtained disaccharide and monosaccharide by mass spectrometry with the mass spectrometry device, iii. analysis by infrared (IR) vibrational spectroscopy of each previously separated disaccharide and monosaccharide with the electromagnetic radiation source, iv. identification of the structure of each disaccharide and monosaccharide by comparison of the obtained IR spectra with a set of reference disaccharide and monosaccharide IR spectra contained in the database, and v. definition of the oligosaccharide sequence by combination of the structures identified for each disaccharide and monosaccharide by the processing means.

In particular, the electromagnetic radiation source is a L.A.S.E.R. source. The electromagnetic radiation source is advantageously integrated into the mass spectrometry device.

DESCRIPTION OF THE FIGURES

FIG. 2 shows the production of the set of constituent monosaccharide fragments (labelled a, b, c, d) and disaccharide fragments (labelled a-b, b-c, c-d) of the tetrasaccharide (labelled 0) by several mass spectrometry steps MS".

FIG. 3 shows the analysis of each of the monosaccharide fragments by IRMPD spectroscopy (top boxes) and their comparison with the reference spectra with which the fragment spectra were identified (bottom boxes).

FIG. 4 shows the analysis of each of the disaccharide fragments by IRMPD spectroscopy (top boxes) and their comparison with the reference spectra with which the fragment spectra were identified (bottom boxes).

EXAMPLES

1. Materials and Methods

Materials

The materials used to implement the method of the invention include a commercial ion-trap mass spectrometer equipped with an electrospray ion source (Thermofinnigan LCQ). This device is modified to allow the injection of an infrared L.A.S.E.R. beam generated by a YAG—pumped tunable OPO/OPA system (LaserVision) at a rate of 10 Hz. It is notably described in Schindler, B. et al. (*Phys. Chem. Chem. Phys.* 2014, 16, 22131-22138)

Fragmentation

Fragmentation of the samples is done by the CID method, in several successive fragmentation steps if need be.

Sampling and IR Spectroscopy

The method of sample preparation by MS" and IRMPD spectroscopy is that described in Schindler, B. et al. (*Phys. Chem. Chem. Phys.* 2014, 16, 22131-22138).

2. Analysis of a Tetrasaccharide

Figure 1:
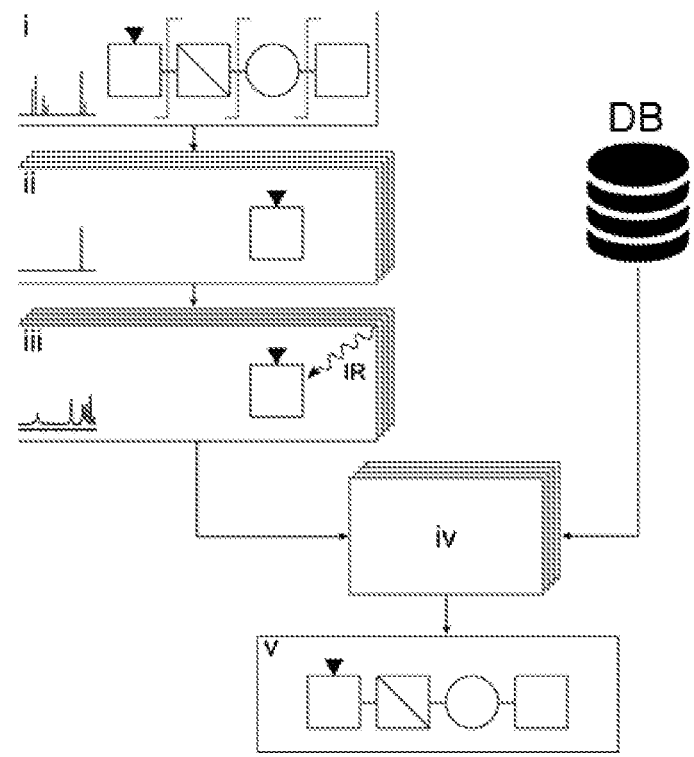
FIG. 1 is a schematic representation of the implementation of the method according to the invention: (i) fragmentation of the oligosaccharide by mass spectrometry, (ii) separation of each of the fragments preparatory to IR spectroscopy analysis, (iii) IR spectroscopy analysis, (iv) identification of the structure of each constituent monosaccharide and disaccharide by comparison with the reference IR spectra contained in the database DB, (v) definition of the sequence by the combinatorial method described in the invention.
Figure 2:
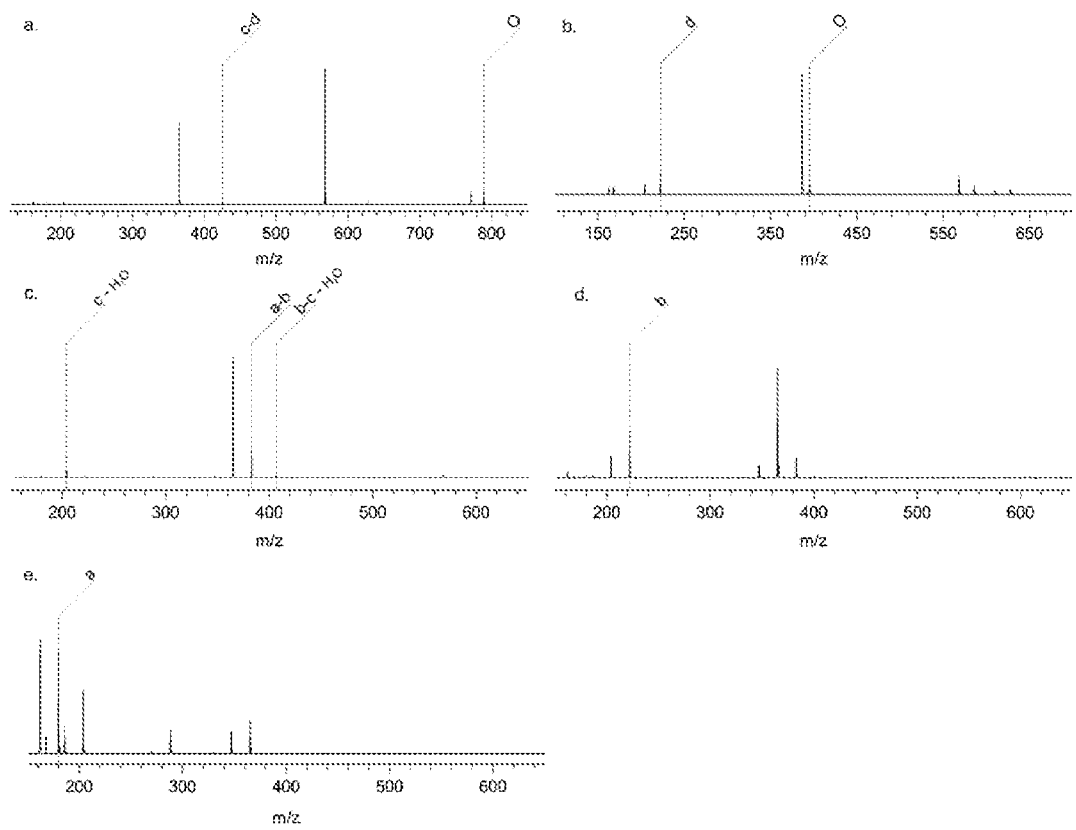
FIGS. 2, 3 and 4 refer to the implementation of the method on the example of the tetrasaccharide GlcNβ(1→4)GlcNAcβ(1→4)GlcNAcβ(1→4)GlcNAc
Figure 3:
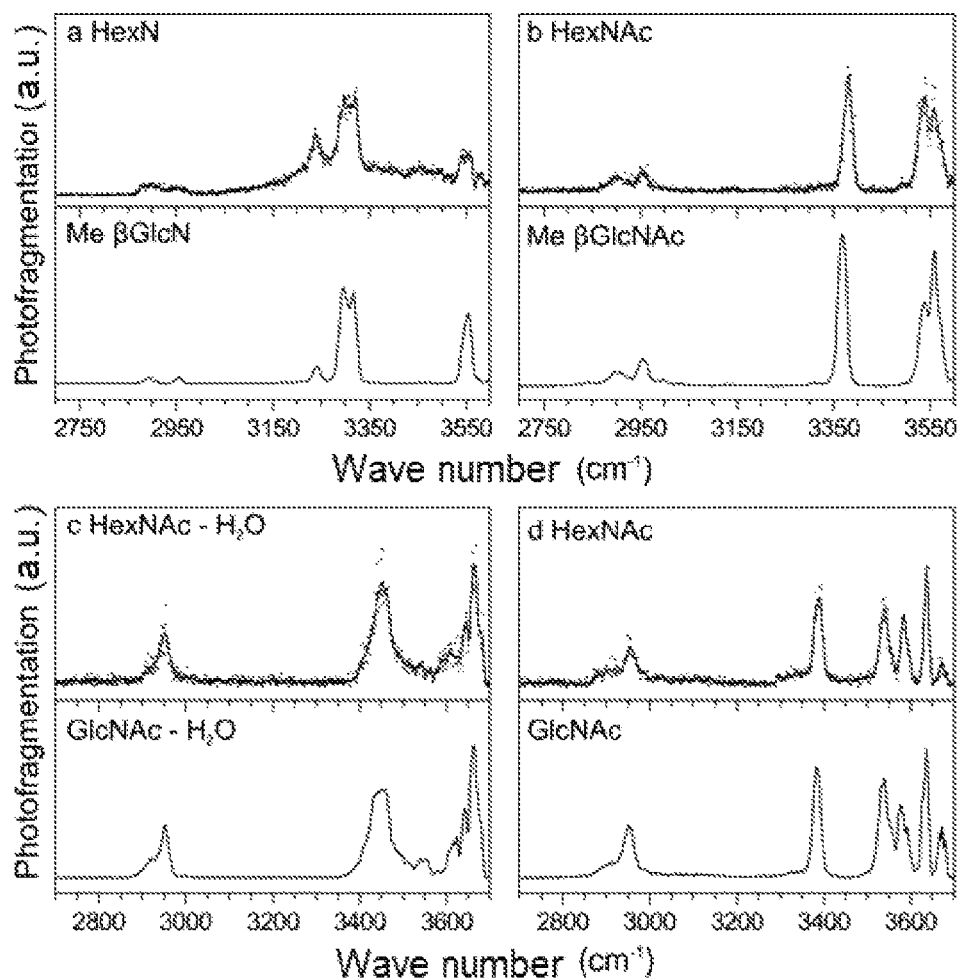
Figure 4:
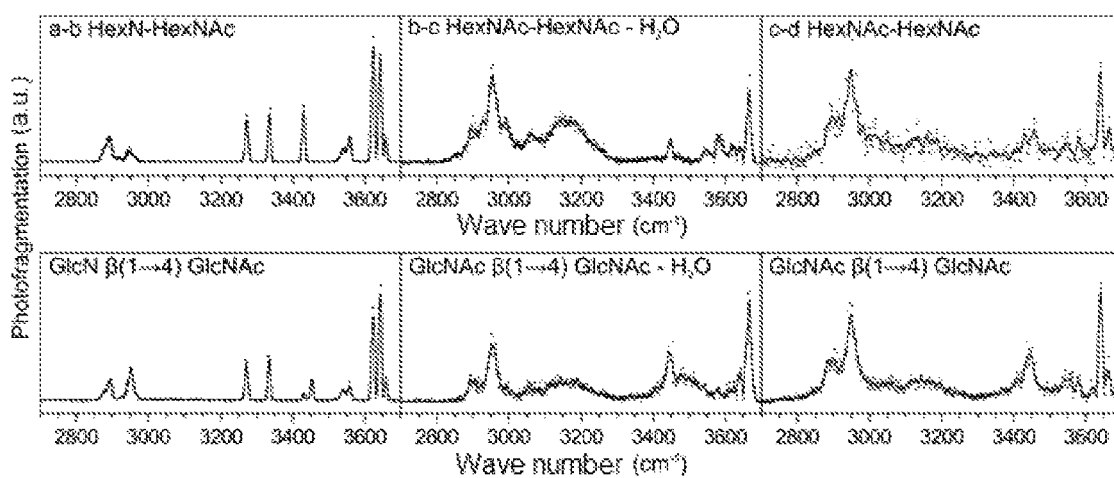

FIGS. 2, 3 and 4 refer to the implementation of the previously described method on the example of the tetrasaccharide

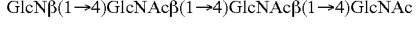

All structural information obtained by comparison of the fragment spectra and the reference spectra is listed in Table 1.

TABLE 1

Identification of the structure of each disaccharide and monosaccharide by comparison of the obtained IR spectra with a set of reference disaccharide and monosaccharide IR spectra.

| Fragment | $MS^n$ | m/z | Generic type | identification |
|---|---|---|---|---|
| | | | identification of monosaccharide structure | |
| a | $MS^4$ | 180 | HexN | β GlcN |
| b | $MS^4$ | 222 | HexNAc | β GlcNAc |
| c | $MS^3$ | 204 | HexNAc—$H_2O$ | GlcNAc—$H_2O$ |
| d | $MS^2$ | 222 | HexNAc | GlcNAc |
| | | | identification of disaccharide structure | |
| a-b | $MS^3$ | 383 | HexN—HexNAc | GlcN β(1→4) GlcNAc |
| b-c | $MS^3$ | 407 | HexNAc—HexNAc—$H_2O$ | GlcNAc β(1→4) GlcNAc—$H_2O$ |
| c-d | $MS^2$ | 425 | HexNAc—HexNAc | GlcNAc β(1→4) GlcNAc |

The oligosaccharide sequence is then obtained by combination of the structural information:

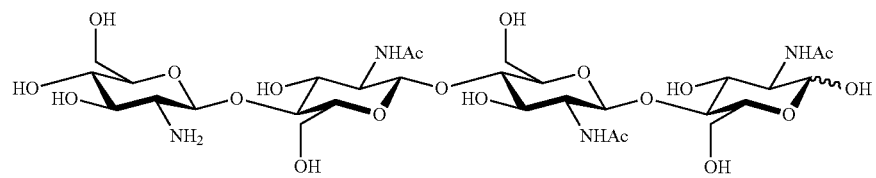

The structure obtained is indeed that of the tetrasaccharide GlcNβ(1→4)GlcNAcβ(1→4)GlcNAcβ(1→4)GlcNAc.

REFERENCES

Both, P. et al., Discrimination of epimeric glycans and glycopeptides using IM-MS and its potential for carbohydrate sequencing. *Nat. Chem.* 2013, 6, 65-74.

Gaye, M. M. et al., Multidimensional Analysis of 16 Glucose Isomers by Ion Mobility Spectrometry. *Anal. Chem.* 2016, 88, 2335-2344.

Nagy, G.; Pohl, N. L. B., Monosaccharide identification as a first step toward de novo carbohydrate sequencing: Mass spectrometry strategy for the identification and differentiation of diastereomeric and enantiomeric pentose isomers. *Anal. Chem.* 2015, 87, 677-685.

Nagy, G.; Pohl, N. L. B., Complete Hexose Isomer Identification with Mass Spectrometry. *J. Amer. Soc. Mass Spectrom.* 2015, 26, 677-685.

Schindler, B. et al., Distinguishing isobaric phosphated and sulfated carbohydrates by coupling of mass spectrometry with gas phase vibrational spectroscopy. *Phys. Chem. Chem. Phys.* 2014, 16, 22131-22138

Stefan, S. et al., Differentiation of Closely Related Isomers: Application of Data Mining Techniques in Conjunction with Variable Wavelength Infrared Multiple Photon Dissociation Mass Spectrometry for Identification of Glucose-Containing Disaccharide Ions. *Anal. Chem.* 2011, 83, 8468-8476

The invention claimed is:

1. A method for sequencing oligosaccharides, wherein it comprises the steps of
   i. fragmentation of the oligosaccharides into disaccharides and monosaccharides while preserving the molecular structure of the constituents as present in the oligosaccharide to be sequenced
   ii. separation of each previously obtained disaccharide and monosaccharide by mass spectrometry,
   iii. analysis by infrared (IR) vibrational spectroscopy of each previously separated disaccharide and monosaccharide,
   iv. identification of the structure of each disaccharide and monosaccharide by comparison of the obtained IR spectra with a set of reference disaccharide and monosaccharide IR spectra, and
   v. definition of the oligosaccharide sequence by combination of the structures identified for each disaccharide and monosaccharide.

2. The method according to claim 1, wherein the fragmentation of the oligosaccharides into disaccharides and monosaccharides (step i.) is done by mass spectrometry.

3. The method according to claim 1, wherein the fragmentation by mass spectrometry is done by CID, CAD, SID, ETD, ECD and laser-induced fragmentation.

4. The method according to claim 1, wherein the IR spectroscopy is performed at a wavelength ranging from 4000 to 2000 $cm^{-1}$.

5. The method according to claim 1, wherein the IR spectroscopy is done by the IRMPD method implemented in an ion trap.

6. An apparatus for sequencing oligosaccharides comprising a mass spectrometry device, an electromagnetic radiation source, a database and processing means, wherein it comprises a processor for controlling the steps of
   i. fragmentation of the oligosaccharides into disaccharides and monosaccharides while preserving the molecular structure of the constituents as present in the oligosaccharide to be sequenced
   ii. separation of each previously obtained disaccharide and monosaccharide by mass spectrometry with the mass spectrometry device,
   iii. analysis by infrared (IR) vibrational spectroscopy of each previously separated disaccharide and monosaccharide with the electromagnetic radiation source, iv. identification of the structure of each disaccharide and monosaccharide by comparison of the obtained IR spectra with a set of reference disaccharide and monosaccharide IR spectra contained in the database, and
v. definition of the oligosaccharide sequence by combination of the structures identified for each disaccharide and monosaccharide by the processing means.

7. The apparatus according to claim 6, wherein the electromagnetic radiation source is a L.A.S.E.R. source.

8. The apparatus according to claim 6, wherein the electromagnetic radiation source is integrated into the mass spectrometry device.

* * * * *